(12) United States Patent
Müller-Schulte

(10) Patent No.: US 7,919,333 B2
(45) Date of Patent: Apr. 5, 2011

(54) SPHERICAL AND MAGNETICAL SILICAGEL CARRIERS HAVING AN INCREASE SURFACE FOR PURIFYING NUCLEIC ACIDS

(75) Inventor: Detlef Müller-Schulte, Aachen (DE)

(73) Assignee: MagnaMedics GmbH, Aachen (DE)

( * ) Notice: Subject to any disclaimer, the term of this patent is extended or adjusted under 35 U.S.C. 154(b) by 1075 days.

(21) Appl. No.: 10/580,733

(22) PCT Filed: Nov. 23, 2004

(86) PCT No.: PCT/EP2004/013260
§ 371 (c)(1),
(2), (4) Date: May 25, 2006

(87) PCT Pub. No.: WO2005/052581
PCT Pub. Date: Jun. 9, 2005

(65) Prior Publication Data
US 2007/0087385 A1  Apr. 19, 2007

(30) Foreign Application Priority Data
Nov. 25, 2003  (DE) .................................. 103 55 409

(51) Int. Cl.
*G01N 33/553* (2006.01)
*G01N 33/53* (2006.01)
(52) U.S. Cl. ........................................ 436/526; 436/518
(58) Field of Classification Search .................. 436/526, 436/525, 518
See application file for complete search history.

(56) References Cited

U.S. PATENT DOCUMENTS

| | | | |
|---|---|---|---|
| 3,917,538 A | 11/1975 | Rosensweig | 252/62.51 |
| 4,070,286 A | 1/1978 | Iler et al. | 210/31 |
| 4,105,426 A | 8/1978 | Iler et al. | 65/18 |
| 4,152,210 A | 5/1979 | Robinson et al. | 195/63 |
| 4,280,918 A | 7/1981 | Homola et al. | 252/62.51 |
| 4,329,241 A | 5/1982 | Massart | 252/62.52 |
| 4,343,901 A | 8/1982 | DeFilippi | 435/176 |
| 4,628,037 A | 12/1986 | Chagnon et al. | 436/526 |
| 4,699,717 A | 10/1987 | Riesner et al. | 210/635 |
| 4,827,945 A | 5/1989 | Groman et al. | 128/653 |
| 4,927,749 A | 5/1990 | Dorn | 435/2 |
| 4,927,750 A | 5/1990 | Dorn | 435/2 |
| 5,209,998 A | 5/1993 | Kavassalis et al. | 430/106 |
| 5,320,944 A | 6/1994 | Okada et al. | 435/7.94 |
| 5,648,124 A | 7/1997 | Sutor | 427/475 |
| 5,746,999 A | 5/1998 | Gries et al. | 424/9.322 |
| 6,103,379 A | 8/2000 | Margel et al. | 428/403 |
| 6,133,047 A | 10/2000 | Elaissari et al. | 436/526 |
| 6,204,033 B1 | 3/2001 | Müller-Schulte | 435/181 |
| 6,255,477 B1 | 7/2001 | Kleiber et al. | 536/25.4 |
| 6,372,517 B1 | 4/2002 | Lange | 436/526 |
| 6,454,143 B1* | 9/2002 | Young | 222/565 |
| 6,514,688 B2 | 2/2003 | Müller-Schulte | 435/4 |
| 6,545,143 B1 | 4/2003 | Harttig et al. | 536/25.4 |
| 6,870,047 B2 | 3/2005 | Kleiber et al. | 536/25.4 |
| 2001/0014468 A1 | 8/2001 | Müller-Schulte | 435/181 |
| 2001/0014650 A1* | 8/2001 | Smith et al. | 502/401 |
| 2002/0064502 A1 | 5/2002 | Gries et al. | 424/9.322 |
| 2002/0136693 A1 | 9/2002 | Gries et al. | 424/9.36 |
| 2002/0137920 A1 | 9/2002 | Kleiber et al. | 536/25.4 |
| 2003/0125542 A1 | 7/2003 | Harttig et al. | 536/25.4 |
| 2003/0135038 A1 | 7/2003 | Kleiber et al. | 536/25.4 |
| 2003/0148101 A1 | 8/2003 | Sauer et al. | 428/404 |
| 2005/0266429 A1 | 12/2005 | Kleiber et al. | 435/6 |

FOREIGN PATENT DOCUMENTS

| | | |
|---|---|---|
| CH | 625 973 A5 | 10/1981 |
| DE | 32 11 309 A1 | 9/1983 |
| DE | 35 08 000 A1 | 9/1986 |
| DE | 37 17 209 A1 | 12/1988 |
| DE | 198 00 294 A1 | 7/1999 |
| DE | 100 35 953 A1 | 1/2002 |
| EP | 0 275 285 B1 | 7/1988 |
| EP | 0 343 934 B1 | 11/1989 |
| GB | 1 439 031 A | 6/1976 |
| JP | 102 14 710 A | 8/1998 |
| WO | WO 91/12079 A1 | 8/1991 |
| WO | WO 94/26379 A1 | 11/1994 |
| WO | WO 96/11054 A2 | 4/1996 |
| WO | WO 96/41811 A1 | 12/1996 |
| WO | WO 97/04862 A1 | 2/1997 |
| WO | WO 97/34150 A1 | 9/1997 |
| WO | WO 97/45202 A1 | 12/1997 |
| WO | WO 98/12717 A1 | 3/1998 |
| WO | WO 98/58257 A1 | 12/1998 |
| WO | WO 99/13993 A1 | 3/1999 |
| WO | WO 99/36359 A1 | 7/1999 |

(Continued)

OTHER PUBLICATIONS

Feng et al. Preparation of the SnO2/Sio2 xerogel with a large specific surface area. Elsevier Science ; Materials Letters 57 (2003) 2409-2412.*

(Continued)

*Primary Examiner* — Jacob Cheu
*Assistant Examiner* — Pensee T Do
(74) *Attorney, Agent, or Firm* — Davidson, Davidson & Kappel, LLC

(57) ABSTRACT

The invention relates to spherical and magnetic silicagel particles which are provided with an increased surface by incorporating $SiO_2$ colloids and produced by a method for inverse dispersion cross-linking of silica sols. The addition of certain metallic oxides to said silica sols and a subsequent tempering make it possible to obtain silicagel particles which exhibit increased nucleic acid binding properties and are used for separating a nucleic acid and isolating biomolecules.

19 Claims, No Drawings

FOREIGN PATENT DOCUMENTS

| | | |
|---|---|---|
| WO | WO 00/32762 A1 | 6/2000 |
| WO | WO 02/09125 A1 | 1/2002 |

OTHER PUBLICATIONS

English translation of WO 02/09125 Muller Schulte, Jan. 31, 2002.*

Alderton et al.: "Magnetic Bead Purification of M13 DNA Sequencing Templates," Anal. Biochem., vol. 201, 166-169, 1992.

Goetz et.al.: "A Novel Magnetic Silica Support for Use in Chromatographic and Enzymatic Bioprocessing," Biotechnology & Bioengineering, vol. 37, 614-626, 1991.

Homola et al.: "Novel Magnetic Dispersions using Silica Stabilized Particles," IEEE Transactions on Magnetics, vol. 22, 716-719, 1986.

Stöber et.al.: "Controlled Growth of Monodisperse Silica Spheres in the Micron Size Range," Journal of Colloid and Interface Science., vol. 26, 62-69, 1968.

Flachsbart et al.: "Preparation of Radioactively Labeled Monodisperse Silica Spheres of Colloidal Size," Journal of Colloid and Interface Science, vol. 30, 568-573, 1969.

Sambrook et.al., Molecular Cloning, A laboratory manual, 2nd Edition, Cold Spring Harbour Lab. Press, Cold Spring Harbour, NY, Protocol 9, 1.62-1.64, Protocol 5, 5.26-5.28, Protocol 13, 5.61-5.64 (10 pages).

Shinkai et.al.: "Preparation of Fine Magnetic Prticlies and Application for Enzyme Immobilization," Biocatalysis, vol. 5, 61-69, 1991.

Kondo et.al.: "Development and application of thermo-sensitive magnetic immunomicrospheres for antibody purification," Appl. Microbiol. Biotechn., vol. 41, 99-105, 1994.

Yanase et al.: "Preparation of Magnetic Latex Particles by Emulsion Polymerization of Styrene in the Presence of a Ferrofluid," Journal of Applied Polymer Science, vol. 50, 765-776, 1993.

Margel et al.: "Novel Effective Immunoadsorbents Based on Agarose-Polyaldehyde Microsphere Beads: Synthesis and Affinity Chromatography," Analytical Biochemistry vol. 128, 342-350, 1983.

Margel et al.: "Polyacrolein Microspheres as a New Tool in Cell Biology," J. Cell Sci., vol. 56, 157-175, 1982.

Widder et al.: " Tumor remission in Yoshida sarcoma-bearing rats by selective targeting of magnetic albumin microspheres containing doxorubicin," Proc. Natl. Acad. Sci., vol. 78, 579-581, 1981.

Laane et al.: "Optimization of Biocatalysis in Organic Media," Biocatalysis in organic media, Proceedings of an International Symposium held at Wageningen, The Netherlands, 65-84, 1987.

Tomlinson et al.: "Incorporation of Water-Soluble Drugs in Albumin Microspheres," Methods in Enzymology, vol. 112, 25-31, Part A, 1985.

Nilson et al.: "Tresyl Chloride-Activated Supports for Enzyme Immobilization," Methods in Enzymology, vol. 135, 65-71, Part B, 1987.

Mueller-Schulte et al.: "Novel Magnetic Microcarriers on the Basis of Poly(Vinyl Alcohol) for Biomedical Analysis," Scientific and Clinical Applications of Magnetic Carriers, 93-105, 1997.

Shriver-Lake et al.: "Silane-modified surfaces for biomaterial immobilization," Immobilized biomolecules in analysis, T. Cass and F.S. Ligler/Oxford University Press, 1998, (8 pages).

* cited by examiner

SPHERICAL AND MAGNETICAL SILICAGEL CARRIERS HAVING AN INCREASE SURFACE FOR PURIFYING NUCLEIC ACIDS

BACKGROUND

The present invention relates to magnetic metal(loid) oxide-containing spherical silica gel particles having high nucleic acid binding capacity, to a process for their preparation and to their use in the bioanalytical and diagnostic sector.

Silica particles have been used for years in bioanalysis for removing and purifying nucleic acids, being particularly able because of their specific physicochemical structure to bind these nucleic acids. Such media which can be employed exclusively in column chromatography are described in German patent DE 32 11 309 (corresponding to U.S. Pat. No. 4,699,717).

The PCT application EP99/08996 describes glass-coated pigments for nucleic acid purification which comprise various metal oxides such as zinc, boron, iron, calcium, potassium and/or aluminum. Glass particles having a mica core and incorporated magnetite particles which are, however, prone to rapid sedimentation are revealed in the PCT application EP96/02459. The preparation processes are time-consuming and require technically elaborate spray drying processes. Ideally spherical particles cannot be prepared by these processes.

Anal. Biochem. 201, 166 (1992) and PCT GB91/00212 describe nucleic acid separation processes using magnetic particles which are able to absorb the nucleic acids after a salt-ethanol precipitation. However, these processes do not operate nucleic acid-specifically, i.e. the magnetic particles also absorb other biosubstances in parallel.

Silanized iron oxide particles for immobilizing enzymes are disclosed in U.S. Pat. No. 4,152,210. Ferromagnetic particles likewise for the purpose of enzyme immobilization are described in U.S. Pat. No. 4,343,901 and are prepared by a sol-gel technique.

The PCT application EP97/04828 describes monodisperse magnetic particles which consist of an $SiO_2$ core which acquires magnetic properties by coating with iron oxide. The particles are enabled to bind nucleic acids by subsequent silanization of the iron oxide layer. U.S. Pat. No. 5,320,944 discloses, analogously thereto, magnetic particles which are 0.2-3 µm in size and which acquire magnetic properties by coating a polymer particle with iron oxides. Further coating of the particles with silanes, nylon or polystyrene subsequently allows antibodies to be coupled to the particles for use in immunoassays. Iron oxide particles coated with colloidal $SiO_2$ are disclosed in U.S. Pat. No. 4,280,918.

Magnetic silica hybrid particles consisting of a polystyrene core onto which magnetite and subsequently a silicon layer are polymerized are disclosed in PCT/US 95/12988. The particles are employed for separating antibodies and cells.

Magnetic silica gel particles 20-100 µm in size for enzyme immobilization, which are generated by electrostatic coating of nickel powders with silica sols, have been described by Goetz et al., Biotechn. & Bioengineering, Vol. 37, 614, 1991.

Organosilanized colloidal silica gel particles as biological separation media are disclosed in the PCT application US99/00403, where the stability of the colloids and the mode of silanization have priority. Magnetic particles which comprise a magnetic core material and are coated with an inorganic oxide are disclosed in EP 0 343 934.

Polymer particles coated with a polymer layer comprising magnetic substances, to which a third polymer coating able to interact with biomolecules is applied are described in PCT application FR97/00912.

Pearl luster color pigments which are 10-60 µm in size and which are enveloped with magnetite and are intended for separating biological mixtures are revealed in the PCT application DE97/01300 (corresponding to U.S. Pat. No. 6,372,517).

U.S. Pat. No. 5,648,124 relates to magnetic hybrid particles which consist of a polymer core and which are first coated with a ferrofluid and subsequently coated with a functional polyacrylate.

U.S. Pat. Nos. 6,204,033 and 6,514,688 describe spherical magnetic polyvinyl alcohol-based polymer particles which can be prepared by inverse suspension polymerization within a short time. The polymer particles disclosed therein are, however, unsuitable for nucleic acid purification without extensive derivatization steps because of the physicochemical properties of polyvinyl alcohol.

The particles known in the art have some disadvantages in relation to the removal of nucleic acids, if they are in fact suitable for this application: firstly, a number of support media are not magnetic (U.S. Pat. No. 4,927,750, DE 32 11 309, PCT/US99/00403; PCT/EP94/01378) so that rapid removal of the particles, as is now required in automated routine analyses, is impossible. Secondly, silica- or polystyrene-based magnetic particles which are coated with a magnetic oxide have a high specific density (PCT/EP97/04828, U.S. Pat. No. 4,152,210, EP 3211309, U.S. Pat. No. 5,320,944), resulting in inadequate dispersibility together with rapid settling of the particles. Use of these particles in an immunoassay or nucleic acid assay which is predominantly carried out in suspension is thus adversely affected because additional mechanical mixing is required. The crucial disadvantage of the coated particles is, however, that the metal oxides may, both as core material and as coating material, despite the subsequent silanization, come into direct contact with the analytical solution. This represents a serious problem in the analysis of nucleic acids, e.g. within the framework of PCR, because the polymerases used in PCR may be deactivated in contact with metals.

The processes known in the art for producing the magnetic particles are always very complicated and, without exception, require a production process lasting many hours.

In addition, the PCT application EP01/08392, corresponding to DE 100 35 953 A1, discloses an inverse suspension process for preparing silica particles which is able to avoid the disadvantages evident from the prior art in relation to the material circumstances and/or the expenditure of time and experimental effort. This process, which is incorporated herein by reference, is based on magnetic colloid-containing aqueous silica sols which are dispersed in specific organic phases and are consolidated to spherical gel particles by addition of base during the dispersion procedure. The disadvantage of the silica gels produced by this process is, however, that they are hydrogels which, as a result of the high water content, are very polar or hydrophilic, which adversely affects the nucleic acid binding capacity. In addition, no support modifications specifically assisting nucleic acid binding are described, so that use of the supports in purifying nucleic acids is unsatisfactory because of the low binding capacity.

SUMMARY OF THE INVENTION

Starting from this prior art, the object of the present invention is to provide silica gel particles suitable for purifying nucleic acids, and processes for producing them which overcome the disadvantages of known silica and polymer supports in relation to the preparation-intensive and time-consuming coating techniques and make it possible to produce silica gel-based magnetic particles efficiently.

DETAILED DESCRIPTION

The spherical silica gel particles which are produced by the process of the invention and which have a content of magnetic particles and in which $SiO_2$ colloids and metal oxides are encapsulated have a distinctly increased surface area and have polymer properties which allow nucleic acids to be bound in significant high concentration (>20 mg/g of support).

Preparation of the particles of the invention starts from preformed aqueous silica hydrosols, which are mixed with magnetic colloids or magnetic particles and subsequently polycondensed to spherical polymer particles in heterogeneous phase with addition of base. A heat treatment of the polymer particles may follow to improve the properties further.

The silica sols (hydrosols) employed in the production are prepared by known processes by hydrolyzing alkoxysilanes using dilute mineral acids or organic acids such as, for example, acetic acid or formic acid. The alkoxysilanes are dispersed in water and hydrolyzed by addition of acid, the hydrolysis procedure being speeded up preferably by employing ultrasound which also contributes to better mixing of the initially heterogeneous phase.

The alkoxysilanes used are also esters of silicic acid with aliphatic alcohols such as, for example, methyl, ethyl or propyl esters, singly or as mixtures. Subsequently, condensation to low-polymeric silica hydrosols takes place, and these gradually lead by further polycondensation to more or less viscous sols. Sonication times of from 5 to 30 minutes, depending on the composition, are sufficient, and the sonication times generally decrease as the acid concentration increases. The mineral acids preferably employed for the hydrolysis have a concentration of 0.02 to 1 mole/liter, the proportion of the acids in the mixture being 10-35%, preferably 20-28%, by volume. The carboxylic acids are employed as pure acids, and their content is usually 15-40% by volume.

The composition of the gel is crucially determined by the manner of hydrolysis and polycondensation. Thus, acid catalysis generally leads to higher hydrolysis rates with slow polycondensation, whereas conversely addition of bases promotes polycondensation.

Controlling the hydrolysis and the polycondensation, which can be utilized in a known manner (cf. PCT/EP01/08392) for specific alteration or adjustment of the pore structure of the gels is, however, insufficient to bring about an increase in the surface area making it possible to bind a significant amount of nucleic acid.

This increase in the surface area is surprisingly achieved by adding a previously made $SiO_2$ colloid whose particle sizes are between 50 and 500 nm to the silica sol before suspension.

The preparation of such colloids according to the prior art is sufficiently well known to the skilled worker in the field. This usually entails dispersing a tetraalkyl orthosilicate in an alcoholic ammonia phase. Within a short time, spherical nanoparticles are formed through hydrolysis of the silanes in the dispersion, and their particle sizes are determined by the nature of the reactants employed, their concentration, the solvent, the ratio of the phases to one another and the temperature. Thus, the reaction rates in methanol are usually higher than in n-butanol, and correspondingly reaction in methanol affords the smallest particle sizes compared with higher alcohols. The influence of the alkoxysilanes on the particle sizes is generally known, the particle size increasing on passing from methyl esters to higher molecular weight esters. The particle sizes can also be influenced in a similar way by varying the ammonia concentration: the particle size usually decreases as the concentration increases. Particles with a size between 50 and 500 nm are selectively formed, depending on the reaction conditions, by means of this process.

By admixing the $SiO_2$ colloids with the silica sols, in the subsequent bead production in suspension the silica colloids are surprisingly integrated into the silica beads in such a way that the resulting particles have an accessible surface area which is a factor of 2 to 5 larger than silica particles known in the art (PCT/EP01/08392).

The concentration of the added $SiO_2$ colloids is usually 10 to 40% by volume, preferably 20 to 35% by volume, based on the hydrosol phase, and the $SiO_2$ colloids have a solids content of 10 to 50% by weight.

Apart from addition of $SiO_2$ colloids as parameter for increasing the nucleic acid binding, it has surprisingly emerged that the presence of certain metal oxides or metalloid oxides in the silica supports also has an additional positive effect in relation to the nucleic acid binding. Oxides which have proved to be particularly efficient in this regard are those of the metals titanium, copper, cobalt, aluminum, calcium, zirconium, manganese, potassium, barium, magnesium and/or zinc, and of the metalloids boron and arsenic, but this selection should be regarded merely as example and not as restriction of the invention. Particularly preferred in the context of the invention are boron oxide ($B_2O_3$) and zinc oxide. To incorporate the metal oxides, appropriate organometallic compound, e.g. in the form of alkyl derivatives, alcoholates, acetates or alkoxides, are admixed with the hydrosols so that the added metal compound(s) or metalloid compound(s) is/are incorporated as oxide(s) into the silica gel matrix when the hydrosol is converted into the silica gel.

From the viewpoint of the intention to improve the nucleic acid binding compared with the support media known from the prior art, in particular silica supports with a defined boron oxide and zinc oxide content have proved to be particularly suitable. In this connection, the boron oxide content is preferably 5-15 mol % and the zinc oxide content is 2 to 10 mol % (based on the silica content). The concentrations of the other metal oxides are usually in the range from 1 to 20 mol %. The incorporation of, in particular, boron oxides and zinc oxides has made it possible to increase the nucleic acid binding by more than 25% compared with prior art supports. Integration of the metal oxides into the $SiO_2$ matrix generally takes place by mixing the appropriate organic components together with the hydrosol formed. The corresponding oxides are then produced in the thermal treatment of the gel described hereinafter.

Beyond the modification steps described above, a further procedure has proved to increase the nucleic acid binding. This relates to a thermal after-treatment of the spherical silica particles (beads) obtained by means of the dispersion crosslinking. The gels known in the art (PCT/EP01/08392) are usually in the form of hydrogels with a high proportion of bound water. The hydrophilic properties, resulting therefrom, of the supports prevent significant nucleic acid binding (i.e. more than 1 mg/g of support) so that they can be used to only a very restricted extent for routine analyses. This disadvantage can now surprisingly be eliminated in the process of the invention by subjecting the hydrogels obtained to a thermal treatment which removes the water completely from the support and thus converts the silica gel particles into solid, anhydrous $SiO_2$ supports which are also generally referred to as xerogels or silica gels. The thermal treatment usually takes place above 250° C., preferably above 500° C., preferably using temperature-controlled muffle furnaces. The thermal treatment usually lasts 1 to 2 hours depending on the size and water content of the polymeric supports.

The particle sizes of the polymer beads produced by inverse dispersion crosslinking can be adjusted both via the viscosity of the aqueous polymer phase and via the mechanical stirring process. Thus, particles with a size of <100 µm are formed predominantly at a viscosity of <40 cp for the sol and particles of >200 µm are formed from sols with a viscosity of >40 cp.

The production of particularly fine particle fractions (<10 µm) requires a preferably commercially available dispersing appliance which operates by the rotor-stator principle (e.g. Ultra-Turrax®) and has a revolving power of >10 000 rpm. Larger polymer beads (>20 µm) can by contrast be produced with conventional stirrers at a stirring speed of 800-5000 rpm. The stirring process usually lasts 3 to 10 seconds. The magnetic particles obtained can subsequently be removed from the dispersion with the aid of a hand magnet and be cleaned by washing with alcohol and water. The silica gel particles obtained in this way preferably have particle sizes between 0.5 and 1 µm, 1 to 10 µm, 10 to 30 µm, 30 to 100 µm and >100 µm.

The obtained gel particles can, following the thermal treatment described above, be used directly in known methods for purifying nucleic acids. In relation to techniques for nucleic acid isolation, reference is made to Sambrook et al.: Molecular Cloning, A Laboratory Manual, 2nd Edition, Cold Spring Harbor Lab. Press, Cold Spring Harbor, N.Y.

In order to confer magnetic properties on the silica beads, magnetic substances are admixed with the silica sols before dispersion in the organic phase. For this are, for example, magnetic colloids or ferrofluids, and ferromagnetic, ferrimagnetic or superparamagnetic microparticles or nanoparticles which have a magnetic moment such that, after encapsulation thereof, the silica beads can be removed with a conventional hand magnet. The colloids or ferrofluids are in some cases commercially available, or their production is described adequately in the literature (see, for example, PCT/EP96/02398 and literature cited therein) and can be accomplished at any time by a worker skilled in this art.

The decisive criterion for the selection of suitable colloids or ferrofluids is the possibility of homogeneously dispersing them in the silica sol, i.e. the magnetic colloid must not flocculate or agglomerate in contact with the sol phase. Particularly suitable for this purpose are in particular ferrofluids which comprise charged surfactants, e.g. in the form of aromatic or aliphatic sulfonic acid derivatives or aliphatic carboxylic acids for stabilization. Such magnetic substances are also, as mentioned above, commercially available.

The possibility of easily and specifically adjusting the magnetic content in the silica gel particle of the invention by admixing the magnetic colloid, which distinguishes this process from the prior art, opens up a wide range of applications which extends far beyond the mere fractionation of biomolecules and nucleic acids or the analysis of biomolecules, as described in PCT/EP01/08392 and the literature cited therein.

Besides the magnetic colloids or ferrofluids which are in nanoparticulate form, it is also possible in principle to use for the encapsulation magnetic particles which have a solid polymer shell. Such magnetic beads which have a shell of polyvinyl acetate, polyvinyl alcohol, dextran, polyacrolein, polystyrene, albumin or alginate and generally have particle sizes of from 0.05 to 5 µm are known in the art (see, for example, PCT/EP96/02398 and literature cited therein) and are also commercially available inter alia under the names Dynabeads, BioMag, Estapor, M-PVA, AGOWA, BioBeads or SPHERO, where in some cases registered trademarks are involved. These magnetic particles are employed in an analogous manner like the colloids or ferrofluids for producing the silica particles of the invention.

After addition of the magnetic colloids, of the $SiO_2$ colloids which increase the surface area, and of the metal compounds to the silica sol, the mixture is dispersed in an organic dispersant. Dispersants suitable for this purpose are solvents which are immiscible with the hydrosol phase and in which the hydrosol phase is able to form stable, defined droplets. Examples thereof are hexane, petroleum ether, toluene, tetrachloromethane, chloroform, trichloro-ethylene, 1,1,1-trichloroethane, heptane or octane. Suitable and preferred solvents are those having a partition coefficient (as defined by C. Laane et al., "Biocatalysis in Organic Media", Laane et al. Editors, Elsevier, Amsterdam, pp. 65, 1987) of >2. Mixtures of the above solvents with a density of about 1 g/cm³ are also very suitable for the dispersing.

To increase the quality of the silica dispersions in relation to uniformity and spherical shape, it has surprisingly proved to be advantageous to add one or more emulsifiers or surfactants to the organic phase. These include surface-active substances or surfactants and stabilizers such as, for example: propylene oxide-ethylene oxide block copolymers, polyglycerol esters, polyoxyethylene sorbitan fatty acid esters, alkylphenyl polyethylene glycol derivatives, polyethylene glycol-castor oil derivatives, block copolymers of castor oil derivatives, polyethylene glycol ether derivatives, polyoxypropylene-ethylenediamine block copolymers, sorbitan fatty acid esters, polyethylene glycols, polyoxyethylene-, modified polyesters, polyoxyethylene alcohol derivatives, polyhydroxy fatty acid-polyethylene glycol block copolymers. Substances of this nature are commercially available on the market inter alia under the proprietary name: Synperonic®, Arlacel®, Brij®, Renex®, Estol®, Eumulgin®, Pluronic®, Triton®, Pripol®, Hypermer®, Span®, Tween®, Tetronic®, Prisorine®, Dehymuls® or Lameform®.

The emulsifier concentrations relevant for producing the magnetic particles are between 0.1 and 15% by weight, preferably between 0.5 and 5% by weight, based on the dispersant.

As alternative to classical organic solvents as dispersing medium it is also possible to employ conventional vegetable oils having a viscosity of from 50 to 500 cp, and mixtures of vegetable oils with the organic solvents. The use of organic solvents has the advantage over the oils, however, that these have a lower viscosity, thus making it possible to carry out the separation of the silica particles from the reaction mixture and the subsequent washing processes within a few seconds with the aid of a commercial hand magnet. In the case of the oils, the separation, including the washing processes, would take considerably longer (in some cases hours). A further advantage is the possibility of recovering the organic liquids by redistillation.

The ratio of organic phase to hydrosol is usually from 5:1 to 30:1 by volume, the ratio of hydrosol to magnetic colloid is from 2:1 to 4:1 by volume, with the content of the magnetic solid in the sol mixture being 15-50% by weight.

In the last step in the synthesis, the silica sols comprising the magnetic colloids, $SiO_2$ colloids and metal compounds are consolidated during the dispersion process to defined spherical silica particles by adding a base. The addition of base leads within a short time (preferably 3 to 20 seconds, generally less than 60 seconds) to a consolidation (gel formation) of the polymer droplets. The rate of gel formation in this case increases with the concentration of the base employed. The bases preferably employed are ammonia or NaOH. Sodium hydroxide solution is usually employed as 0.05 to 0.1 molar solution, and ammonia in the form of a 1 to 12% strength aqueous solution. The ratios of base to sol are normally from 1:2 to 1:4 by volume.

Since the gelation reaction proceeds very quickly, the time required to be expended in the production process for the basic particles including the synthesis of the sol and of the magnetic colloid is less than 1 hour. This means a saving of time of at least 30 to 90% compared with all conventional processes.

Besides the use of the silica gel beads of the invention with increased surface area specifically for purifying nucleic acids, the silica gels can additionally be modified so that their use in separation technology can be significantly extended. It is known from patents DE 32 11 309 (corresponding to U.S. Pat. No. 4,699,717), cited here as reference, that in particular media having cationic groups (anion exchangers) are outstandingly suitable for fractionating nucleic acids and proteins. Such a type of support can be produced by chemical reaction of the silica gel particles with epoxy-substituted alkoxysilane such as, for example, 3-glycidyloxypropyltrimethoxysilane or 3-glycidyloxypropylmethyldiethoxysilane and subsequent nucleophilic opening of the oxirane ring using tertiary or secondary alkylamines. It is also possible to synthesize strongly and weakly acidic ion exchangers and metal chelate supports by reacting the described epoxy-substituted silica gel particles with the aid of carboxylic acids, sulfites, thiosulfates and amino-substituted carboxylic acids, e.g. nitrilotriacetic acid or iminodiacetic acid.

Functionalization of the basic silica beads to specific support systems is not just limited to the synthesis of ion exchangers. In a particular embodiment, the $SiO_2$ supports can be reacted with substituted alkylalkoxysilanes of the general formula $X-(CH_2)_n-Si-(OR)_3$, where X is a halogen, cyano, $NH_2$ or mercapto radical, n=1-6, preferably 3, R is an alkyl, trialkylsilyl radical or H. Ligands in the form of peptides, proteins or enzymes can be covalently bonded to the supports modified in this way, whether for separation according to the affinity principle or for use as biocatalysts. Proteins and other ligands can moreover be coupled directly by simple incubation with the halogen-substituted supports.

Without going into further detailed explanations concerning these couplings and modifications, which are described inter alia in "Methods in Enzymology", Vol. 135, Part B, edited by K. Mosbach, Academic Press, Orlando, 1987, in "Scientific and Clinical Applications of Magnetic Carriers", Hatfeli et al. (Editors), Plenum Press, New York, 1997, and in "Immobilized Biomolecules in Analysis", T. Cass and F. S. Ligler Editors, Oxford University Press, 1998, it is assumed that a person skilled in this art knows the specific reaction methods sufficiently well and therefore can utilize the description in principle. The described embodiments are therefore by no means to be interpreted as limiting disclosures.

The processes and products of the invention are described in detail in the examples which follow.

Example 1

Preparation A: 5 ml of tetraethoxysilane are mixed with 37 ml of propanol and rapidly stirred with a solution consisting of 1.9 ml of 25% strength ammonia and 3.7 ml of water. After 30 minutes, $SiO_2$ colloids with an average particle size of 223 nm result. The colloid is subsequently centrifuged down and the supernatant is pipetted off. The precipitate is dried under oil pump vacuum for 5 minutes, taken up in 5 ml of water and redispersed with uses of an ultrasonic bath.

Preparation B: A mixture of 90 ml of tetraethoxysilane, 10 ml of water and 8.5 ml of 0.1M HCl are sonicated in an ultrasonic bath until a homogeneous mixture forms (about 20 minutes).

Then 25 ml of a magnetic colloid which has been prepared by the method of Shinkai et al. (Biocatalysis, Vol 5, 61, 1991) by oxidizing a 0.6 molar iron(III) salt solution which by use of 0.3M Na nitrite are added to preparation B. This is followed by a brief sonication in the ultrasonic bath for 2 minutes. The resulting magnetic dispersion is then mixed with 5 ml of preparation A and 6.5 g of zinc 2,2,6,6-tetramethyl-3,5-heptanedionate and again sonicated for 2 minutes. The resulting dispersion is introduced into one liter of trichloroethylene in which 2.5% by weight of Brij 52 and 1.8% by weight of Tween 85 are dissolved. The dispersion is dispersed with agitation (1500 rpm) for some seconds and then 45 ml of 1% strength ammonia solution are added. Agitation is continued for 5 seconds. After 5 minutes, the magnetic particles are removed from the dispersion with the aid of a commercial hand magnet and washed 5 times each with about 50 ml of methanol and water. Magnetic particles with an average particle size of 38 μm are obtained. After incubation in water for 12 hours, the particles are again washed several times with water and subsequently dried in vacuo for about 1 hours. The particles are then heated in a muffle furnace at 650° C. for 1 hour. The magnetic particles obtained in this way can be used by known methods for purifying nucleic acids.

Example 2

Preparation A: An $SiO_2$ colloid is prepared from a mixture consisting of 0.63 ml of water, 2.35 ml of saturated aqueous ammonia solution, 0.3 ml of tetra-ethoxysilane and 1.69 ml of ethanol. Particles with an average size of 245 nm result. Further vacuum treatment and working up and redispersion of the colloid takes place in analogy to example 1.

Preparation B: A mixture consisting of 100 ml of tetra-ethoxysilane, 20 ml of water and 5 ml of 0.05M HCl is homogenized with the aid of an ultrasonic bath. 30 ml of magnetic colloid (analogous to example 1) are admixed with this sol phase and treated in an ultrasonic bath for 2 minutes. This dispersion is subsequently mixed with preparation A and with 4.8 g of zinc acetate and sonicated for 5 minutes.

The resulting dispersion is introduced into 3 liters of trichloroethylene in which 3.5% by weight of Span 60 and 1.5% by weight of Tween 85 are dissolved, and dispersed by agitation (2500 rpm) for 4 seconds. 55 ml of 1% strength ammonia solution are immediately added. Agitation is continued for 5 seconds. After 5 minutes, the magnetic particles are removed from the dispersion with the aid of a commercial hand magnet and washed five times each with about 50 ml of methanol and water. Magnetic particles with an average particle size of 24 μm are obtained. After incubation in water for 12 hours, the particles are again washed several times with water and subsequently dried in vacuo for about one hours. The particles are subsequently heated in a muffle furnace at 650° C. for 2 hours. The magnetic particles obtained in this way can be employed in known methods for isolating nucleic acids from biological fluids.

Example 3

25 ml of tetraethoxysilane are mixed with 7.5 ml of water and 2.5 ml of 0.15M HCl and homogenized in analogy to example 1. 12 ml of ferrofluid EMG 507 (from FerroTec, Nashua, USA), 4.5 ml of triethyl borate, 2.8 ml of $SiO_2$ colloid which was synthesized in analogy to example 1, and 0.8 g of zinc 2,2,6,6-tetramethyl-3,5-heptanedionate are added to this sol phase. The mixture is sonicated in an ultrasonic bath while cooling in ice for 5 minutes. The dispersion is subsequently dispersed with agitation (1800 rpm) in 450 ml of hexane in which 1.5% by weight of Span 80 and 4.5% by weight of Dehymuls HRE are dissolved. During the dispersion process, 12 ml of 1% strength ammonia solution are added. Agitation is continued for 5 seconds. Separation and working up of the obtained magnetic particles takes place in analogy to example 1. The resulting supports have an average particle size of 84 µm. The removed magnetic particle fraction is washed with methanol and water in analogy to examples 1. This is followed by washing several times with 30 ml of dry toluene each time, with subsequent vacuum drying for two hours. The resulting product is then heated in a muffle furnace at 120° C. for 3 hours and subsequently at 650° C. for a further 1 hours. The product is subsequently heated under reflux with addition of 25 ml of toluene dried over molecular sieves and 0.5 g of 3-aminopropyltriethoxysilane for 12 h. The magnetic particles are again removed magnetically and washed five times each with toluene and chloroform. This is followed by drying in vacuo for several hours. The amino-modified product is subsequently reacted with 6% strength glutaraldehyde solution in 10 ml of 0.1M Na carbonate buffer, pH 9.2, at 35° C. for 3 hours. It is subsequently thoroughly washed with 0.1M phosphate buffer, pH 7.2. The aldehyde-functionalized magnetic particles obtained are suspended in 8.5 ml of 0.1M phosphate buffer and incubated in 2 ml of 0.1M phosphate buffer, pH 7.2, in which 5.5 mg of streptavidin are dissolved. After reaction at 40° C. for six hours, the product is washed five times with phosphate buffer. In order to saturate remaining residual aldehyde groups, the magnetically removed product is incubated in 10 ml of 0.2M ethanolamine at room temperature over a period of 5 hours. The magnetic particles which have subsequently been washed several times with phosphate buffer can be used directly by known processes for binding biotinylated nucleic acids or biotinylated proteins.

What is claimed is:

1. A process for producing spherical magnetic silica gel particles comprising:
   a) converting alkoxysilanes into a hydrosol by acid catalysis with an acid as spherical magnetic silica gel particle precursors and then
   b) obtaining a hydrosol mixture by
      i) admixing a SiO2 colloid with the hydrosol;
      ii) adding magnetic particles to the hydrosol; and
      iii) adding one or more compounds in the form of oxides selected from the group consisting of metal compounds, metalloid compounds, and combinations thereof to the hydrosol; then
   c) dispersing the hydrosol mixture in a dispersant which is immiscible with a phase of the hydrosol mixture and consolidating the hydrosol mixture by addition of a base during the dispersion process to obtain solid spherical magnetic silica gel particles; and
   d) converting the solid spherical magnetic silica gel particles by a thermal treatment to form thermally treated solid spherical magnetic silica gel particles (xerogels); wherein the admixing the SiO2 colloid with the hydrosol increases the surface area of the solid spherical magnetic silica gel particles (xerogels) and the magnetic particles cause the solid spherical magnetic silica gel particles to acquire magnetic properties.

2. The process of claim 1, wherein the ratio of hydrosol to dispersant is from 1:5 to 1:30 by volume and the dispersant is a vegetable oil with a viscosity of from 50 to 500 cp or organic solvents with a partition coefficient of greater than 2 in the octanol/water system, the organic solvents selected from the group consisting of chlorinated hydrocarbons, alkanes with a carbon chain length of more than 7 C atoms, aromatic compounds, and mixtures thereof.

3. The process of claim 1, wherein the dispersion is agitated mechanically with a stirring speed of from 500 to 20 000 rpm and for not longer than 10 seconds so that a predetermined particle diameter in the range from 0.5 to 2000 µm is attained.

4. The process of claim 1, wherein the thermally treated solid spherical magnetic silica gel particle particle diameter is in the range of 0.5 to 1 µm.

5. The process of claim 1, wherein the thermally treated solid spherical magnetic silica gel particle particle diameter is in the range of 10 to 30 µm.

6. The process of claim 1, wherein the thermally treated solid spherical magnetic silica gel particle particle diameter is in the range of 30 to 100 µm.

7. The process of claim 1, wherein the thermally treated solid spherical magnetic silica gel particle particle diameter is greater than 100 µm.

8. The process of claim 1, wherein the alkoxysilanes are orthoesters of silicic acid with aliphatic alcohols having a carbon chain length of from 1 to 5 C atoms.

9. The process of claim 1, wherein the acid in the acid-catalyzed hydrolysis of the alkoxysilanes is selected from the group consisting of dilute mineral acids, organic acids and combinations thereof, and wherein the content of the dilute mineral acids in the hydrosol silane phase is from 10 to 35% by volume, and wherein the content of the organic acids in the hydrosol phase is from 15 to 40% by volume.

10. The process of claim 9, wherein the content of the dilute mineral acids in the hydrosol silane phase is from 20 to 28% by volume.

11. The process of claim 1, wherein the conversion of the alkoxysilanes into the hydrosol is carried out with ultrasound for from 5 to 30 minutes.

12. The process of claim 1, wherein the magnetic particles are selected from the group consisting of magnetic colloids, ferrofluids, ferromagnetic, ferromagnetic, superparamagnetic particles, and combinations thereof.

13. The process of claim 1, wherein the dispersant is admixed with one or more surface-active substances selected from the group consisting of sorbitan fatty acid esters, propylene oxide-ethylene oxide block copolymers, polyglycerol esters, polyoxyethylene sorbitan fatty acid esters, alkylphenyl polyethylene glycol derivatives, polyethylene glycol-castor oil derivatives, block copolymers of castor oil derivatives, polyethylene glycol ether derivatives, polyoxypropylene-ethylenediamine block copolymers, polyethylene glycols, polyoxyethylene-, modified polyesters, polyoxyethylene alcohol derivatives, polyhydroxy fatty acid-polyethylene glycol block copolymers, and combinations thereof, wherein the content of the surface-active substance is from 0.1 to 15% by weight based on the dispersant.

14. The process of claim 1, wherein a 1 to 20% strength base is added during the dispersion process in a volume of from 10 to 30% based on the hydrosol phase.

15. The process of claim 1, wherein the base is ammonia.

16. The process of claim 1, wherein the content of one or more compounds selected from the group consisting of metal compounds, metalloid compounds or combinations thereof in the hydrosol is from 1 to 20 mol %, wherein the metal compounds are selected from the group consisting of zircon, titanium, copper, cobalt, aluminum, calcium, potassium, manganese, barium, magnesium, zinc, and combinations thereof; wherein the metalloid compounds are selected from the boron, arsenic and combinations thereof, and wherein the metal compounds are in the form selected from the group consisting of acetates, fumarates, alcoholates, ethylenediaminetetraacetic acid, nitrilotriacetic acid, alkyl derivatives, porphine derivatives, carboxylate derivatives and combinations thereof.

17. The process of claim 1, wherein the gel particles are subjected to a thermal treatment at temperatures >250° C. over a period of time from one to several hours, and thus are converted into silica gel particles.

18. The process of claim 1, wherein the silica gel particles are further reacted in a process step with substituted alkyl-alkoxy-silanes of the general formula $X-(CH_2)_n-Si-(OR)_3$, wherein X is selected from the group including aldehyde, epoxy, halogen, cyano, $NH_2$ or mercapto radicals;

n=1-6; and

R is an alkyl, trialkylsilyl radical or H.

19. The process of claim 1, wherein the thermally treated solid spherical magnetic silica gel particle particle diameter is in the range of 1 to 10 μm.

* * * * *